US005399349A

United States Patent [19]

Paunescu et al.

[11] Patent Number: 5,399,349

[45] Date of Patent: Mar. 21, 1995

[54] TREATMENT OF ACNE

[76] Inventors: Calin Paunescu, 5030 N. Marine Dr., Apt. 2610, Chicago, Ill. 60640; Tamara Paunescu, Iancu Nicolaie 50, Bucharest, Romania

[21] Appl. No.: 944,218

[22] Filed: Sep. 11, 1992

Related U.S. Application Data

[63] Continuation-in-part of Ser. No. 831,832, Feb. 6, 1992, abandoned.

[51] Int. Cl.[6] .............................................. A61K 35/78

[52] U.S. Cl. .................................. 424/195.1; 514/859

[58] Field of Search ...................... 514/859; 424/195.1

[56] References Cited

U.S. PATENT DOCUMENTS

| | | | |
|---|---|---|---|
| 4,614,652 | 9/1986 | Valyi et al. | 424/195.1 |
| 4,933,177 | 6/1990 | Grollier et al. | 424/74 |

FOREIGN PATENT DOCUMENTS

| | | |
|---|---|---|
| 67357 | 7/1979 | Romania . |
| 81913 | 6/1983 | Romania . |
| 86828 | 4/1985 | Romania . |
| 1243728 | 7/1986 | U.S.S.R. . |

OTHER PUBLICATIONS

Portion of Book entitled: Apifitotherapy in Treatment of Inflammatory Diseases of the Buccal Mucosa, published by Tamara Paunescu in the Romanian language in 1988 (a handwritten translation of the section).

Chem. Abstracts 105(20): 178473f (1986).

Chem. Abstracts 102 (14): 119671j (1983).

Chem. Abstracts 95(6): 49411k (1979).

Chem. Abstracts 104(10): 75063x (1985).

Steinmetz, E. F., Codex Vegetabilis (1957) p. 1188.

Remington's Pharmaceutical Sciences. Fifteenth Edition Mack Publishing Co. 1975. pp. 1519–1522.

*Primary Examiner*—Raymond Henley, III
*Assistant Examiner*—Phyllis G. Spivack
*Attorney, Agent, or Firm*—Gerstman, Ellis & McMillin, Ltd.

[57] ABSTRACT

A patient with acne may be treated by administering to the patient an effective amount of a pharmaceutical composition which comprises a dispersion of propolis in a pharmaceutical carrier as propylene glycol which comprises a neutral buffered plant-extract-based emollient comprising an extract selected from the group consisting of verbascum, gratiola officinalis and combinations thereof and other ingredients as extracts of black honey comb and millefoli.

9 Claims, No Drawings

TREATMENT OF ACNE

CROSS REFERENCE TO RELATED APPLICATION

This application is a continuation-in-part of U.S. application Ser. No. 07/831,832, filed Feb. 6, 1992, now abandoned.

BACKGROUND OF THE INVENTION

Acne is a skin disease that is very resistant to effective treatment, and often results in a scarring which can have a serious psychological effect on the acne patient.

Presently, the cosmetic and pharmaceutical compounds typically used for the treatment of acne, which are often based on antibiotics, give less than satisfactory results, while presenting a certain degree of toxicity and allergic sensitivity, among other undesired side effects. Other pharmaceutical agents, while having less toxicity or allergy problems, are simply ineffective.

In Valyi et al. U.S. Pat. No. 4,614,652, a cosmetic composition is disclosed for the treatment of acne, which comprises an extract of dried chamomile and dried St. John's wort, in combination with an apple and or gooseberry brandy based extract of propolis and a known ceratoplastic agent.

In accordance with this invention, an improved and highly effective treatment for acne is provided, with superior results being obtained on a regular basis over antibiotic regimes, and also with respect to the formulations of the above cited patent. Also, the formulations of this invention are essentially without toxicity and typically without allergic sensitivity, unlike antibiotics.

DESCRIPTION OF THE INVENTION

By this invention, formulations are provided for both the enteral and topical application to an acne patient. Typically, the acne is treated in a patient by simultaneous enteral and topical application, usually with different formulations in accordance with this invention as described below. The term "acne" as used herein may also include other chronic skin inflammatory conditions and infections above and beyond classic acne, since many of such skin conditions are also responsive to treatment by this invention.

Broadly, a patient with acne may be treated by administering to the patient a pharmaceutical composition which comprises 0.5 to 20 weight percent of a dispersion of propolis in a pharmaceutical carrier which comprises a neutral-buffered, plant-extract-based emollient comprising an extract selected from the group consisting of verbascum, gratiola officinalis, and combinations thereof.

The propolis is preferably dispersed in propylene glycol, which is an improved dispersing agent for propolis, so that the formulation may contain 0.4 to 50 weight percent of propylene glycol in the dispersion. Preferably, the pharmaceutical composition used in the method may comprise from 1 to 40 weight percent of a dispersion of 10 parts by weight of propolis in 8 to 12 parts by weight of propylene glycol, with the dispersion being mixed with 70 to 99 weight percent of a pharmaceutical carrier formulation which may comprise the plant extract based emollients as described herein.

In topical formulations, an extract of millefoli may also be present in a concentration of 10 to 30 weight percent. Typically the extract of verbascum is present in a concentration of 1 to 50 weight percent, and the extract of gratiola officinalis is likewise present in a concentration of 1 to 50 weight percent.

When the pharmaceutical composition of this invention is for topical administration, it typically comprises from 0.5 to 40 weight percent of the above propolis-propylene glycol dispersion, with 5 to 30 weight percent of an extract of verbascum and 10 to 30 weight percent of an extract of gratiola officinalis, typically with 10 to 30 weight percent of an extract of millefoli, to form a lotion for topical application.

When the composition of this invention is intended for enteral administration, it preferably comprises from 10 to 30 weight percent of the above propolis propylene glycol dispersion, mixed with an enteral administration carrier which provides a neutral buffer and emollient. In this circumstance the formulation may comprise from 10 to 50 weight percent of an extract of verbascum and 10 to 50 weight percent of an extract of gratiola officinalis as the carrier. Further, the formulation preferably comprises from 15 to 30 weight percent of black honey comb extract.

Each of the above extracts of verbascum, gratiola officinalis, and millefoli as disclosed herein and below are formed by placing the respective plants in a glass container and mixed with about 50 percent ethyl alcohol by weight, being allowed to stand at a temperature of 60 to 70 degrees C. for 15 to 20 days, adding alcohol as needed so that the plants shall be covered at all times. If different alcohol contents or alcohols are used, the above-stated and claimed portions of these extracts in the pharmaceutical compositions may be appropriately adjusted. It is also contemplated that differing times of standing and differing temperatures may be used to prepare the respective extracts of the above three plants. Afterwards, the mixture is filtered, and applied as the respective ingredients to the pharmaceutical compositions.

The propolis exhibits improvements in its dispersion and effect when propylene glycol rather than alcohol, or brandy, is used as the dispersing agent. While a 50 percent dispersion is specifically taught, other concentrations may also be used.

In accordance with this invention, the pharmaceutical composition of this invention is typically administered in at least two and preferably three forms, essentially simultaneously, to the patient. The patient receives the enteral formulation, typically simply by swallowing it. Also, a lotion based on this invention is applied to the acne-affected skin areas and, after application of the lotion to the affected areas and drying of the lotion on the skin, a cream in accordance with this invention is preferably applied.

Typically, 10 to 20 drops of the syrup of this invention is taken orally twice daily for 15 to 21 days, depending upon the severity of the acne. The lotion is applied typically once per day with topical application, typically about 30 drops to cover the face or corresponding area, until it is smoothly rubbed in. Then after drying for 3 to 7 minutes, the cream is applied, as a topical application over the lotion with a gentle massage, once per day. The topical application typically needs to be applied for about 10 to 15 days, which is somewhat shorter than the oral application.

Without wishing to be limited to any theory of operation of the invention of this application, it is believed that a strong synergistic affect against acne takes place with the presence of propolis plus the particular plant extract-based emollients in accordance with this invention, to exert a strong antimicrobial effect such as a bacteriostatic effect both internally and on the skin. It is believed that the formulations of this invention also exhibit significant antimicrobial and anti-viral effect against other organisms besides the organisms involved in acne. The application of two formulations for topical application is believed to provide a double function in that the lotion tends to stop the spread of the acne infection, while the cream is a softening agent that facilitates the removal of pus from the acne and the like.

More specifically, the lotion of this invention may comprise the following ingredients in the following proportions:

| | |
|---|---|
| 1. Verbascum extract | 15–20% by weight |
| 2. Gratiola Officinalis extract | 15–20% by weight |
| 3. Millefoli extract | 15–20% by weight |
| 4. Extract of Propolis (in 50% Propylene glycol) | 10–20% by weight |
| 5. Camphor | 0.5–1% by weight |
| 6. Menthol | 0.5–1% by weight |
| 7. Sterilized water | 15–20% by weight |

The first three items above are preferably used in essentially equal parts.

The resulting lotion is a brown liquid, which is then applied to the skin as discussed above. A preferred application method is to paint the acne-affected skin using cotton rolls, or by using compresses in the most severe cases for lengthy, moist application.

EXAMPLE 1

A specific embodiment of the lotion of this invention is prepared in a mixing tank under sterile conditions, with the following ingredients:

| | |
|---|---|
| 1. Verbascum extract | 20 parts by weight |
| 2. Gratiola Officinalis extract | 20 parts by weight |
| 3. Millefoli extract | 20 parts by weight |
| 4. Extract of Propolis (in 50% Propylene glycol) | 20 parts by weight |
| 5. Camphor | 1 part by weight |
| 6. Menthol | 1 part by weight |
| 7. Sterilized water | 18 parts by weight |

To make the extracts of the verbascum gratiola officinalis, and millefoli plants, the specific technique described above is used here and in the other examples.

In accordance with this invention, the cream discussed above may preferably comprise the following ingredients:

| | |
|---|---|
| 1. Verbascum extract | 10–15% by weight |
| 2. Honey | 1–2% by weight |
| 3. Extract of Propolis (in 50% propylene glycol) | 1–2% by weight |
| 4. Lanolin | 1–2% by weight |
| 5. Cetaceum | 1–2% by weight |
| 6. Cocoa Butter | 1–2% by weight |
| 7. White beeswax | 1–2% by weight |
| 8. Sterilized water | 60–65% by weight |

The cream has a very light yellow color and a pleasant aroma. It is applied to the skin by massage, typically, after application of the lotion and drying of the lotion on the skin. Ingredients 2 and 4 through 7 may be replaced with other, equivalent ingredients, commonly used in lotions.

EXAMPLE 2.

A preferred formulation for the cream of this invention is as follows:

| | |
|---|---|
| 1. Verbascum extract | 15 parts by weight |
| 2. Honey | 2 parts by weight |
| 3. Extract of Propolis | 2 parts by weight |
| 4. Lanolin | 2 parts by weight |
| 5. Cetaceum | 2 parts by weight |
| 6. Cocoa Butter | 2 parts by weight |
| 7. White beeswax | 2 parts by weight |
| 8. Sterilized water | 63 parts by weight |

The verbascum extract is made in a manner similar to that previously described.

The cream may be mixed in a porcelain mortar with all of its ingredients, or in any other desired way.

With the topical application of the lotion and/or the cream, a very accelerated healing of ache can be observed, with the skin regaining its natural aspect, often without scarring or other side effects. However, while the lotion and the cream may be used separately, they are preferred to be used together as described, and they are also preferred to be used in conjunction with the oral treatment with a syrup in accordance with this invention and as described below.

The syrup of this invention may preferably comprise:

| | |
|---|---|
| 1. Gratiola officinalis extract | 20–25% by weight |
| 2. Verbascum extract | 20–25% by weight |
| 3. Black honey comb extract | 20–25% by weight |
| 4. Extract of Propolis | 10–20% by weight |
| 5. Honey | 1–5% by weight |
| 6. Aspirin | 0.5–1% by weight |

EXAMPLE 3.

A preferred example of the syrup is shown as follows:

| | |
|---|---|
| 1. Gratiola Officinalis extract | 25 parts by weight |
| 2. Verbascum extract | 25 parts by weight |
| 3. Black Honey Comb extract | 25 parts by weight |
| 4. Extract of Propolis (in 50% propylene glycol) | 10 parts by weight |
| 5. Honey | 4 parts by weight |
| 6. Aspirin | 1 part by weight |

Aspirin and honey are optional ingredients, the honey being present for taste in part. The verbascum and gratiola officinalis plants, and the black honey comb may be formed into an extract as previously described, being mixed with 50 percent alcohol (ethanol) at a temperature of 60 to 70 degrees C. and maintained for 15 to 20 days, adding alcohol as needed so that the plants shall be covered at all times. Afterwards, the mixtures are filtered and added to the other ingredients of the syrup.

The syrup is given typically orally in a dose of approximately 10 to 20 drops, twice a day, for typically 10 to 15 days. It can be observed to contribute to accelerated healing of acne, without side effects. Additionally, without wishing to be limited to theoretical considerations in this invention, the syrup is believed to provide a significant stimulus to the immunological system generally, by general biostimulating effect, tonic action, and general trophicity. Also, no toxic effects have been noticed from the syrup.

It should be noticed that, while specific examples are disclosed, other proportions of the ingredients are possible and effective, and that the method can be used for various types of skins and types of acne. Some equivalent ingredients to particularly the secondary ingredients disclosed above may also be used in the formulations as well as other desired ingredients such as preservatives, flavoring agents, antibiotics, thickening agents, and the like.

It should be noted that the addition of active ingredients such as bitumen-sulfonic acid ammonium salts, or other sulfur derivatives are unnecessary in this invention to achieve effective cures of acne, contrary to the disclosure of the above-cited patent. However, such sulfur compounds may be added, if desired.

In Romania, 37 acne patients have received treatment under the care of a physician in accordance with this invention, using the oral administration of the syrup of Example 3, coupled with the topical administration of the lotion of Example 1, followed by topical application of the cream of Example 2 on top of the dried lotion.

The cases of acne were admitted for treatment after failure of classical therapy performed in various Romanian clinics.

The group was composed of 11 women and 26 men, with the ages as follows:

| | |
|---|---|
| 10–19 years | 7 patients |
| 20–29 years | 28 patients |
| 30–39 years | 2 patients |

| | |
|---|---|
| Rozace | 14 patients |
| Infected | 16 patients |
| Necrotic | 7 patients |

Clinical investigations performed before the beginning of the treatment showed all patients to be free of diabetes and dislipidemia. Three of the male patients presented a superactivity of the suprarenal gland.

The same method of treatment was used for all patients irrespective of the type of acne or the degree of difficulty. The method was as follows:

Each patient received orally 10 to 20 drops of the syrup of Example 3 twice daily for 15 to 21 days. The lotion was applied to each patient topically on the acne infected areas once per day, about 30 drops of lotion of Example 1 being used for an area the size of the face. Then, after drying for 3 to 7 minutes, the cream of Example 2 was applied. This topical treatment was performed for 10 to 15 days on each patient. Gentle massage was used particularly with the cream.

The patients were seen every few days. Clinical examinations took place for each patient at 13, 30, and 42 days from the beginning of the oral and topical treatment in accordance with this invention.

The criteria used for observation were:

(a) Evolution of Local Lesions (b) General Health of the Patients (c) Weight Gain or Loss (d) Any Complications The total observation of patients was over eight weeks from the beginning of treatment.

The treatment of all of the patients was successful, with healing of the lesions taking place in all patients. The healing of the lesions typically began:

(a) After about eight days for Rozace acne (b) After about fifteen days for Infected acne.

(c) After about twenty-one days for Necrotic acne

Total healing of the lesions took place in 11–29 days for the Rozace patients; in 18–35 days for the infected acne patients; and in 24–42 days for the necrotic acne patients.

After healing had taken place, we did not notice recurrence of the acne in any of the patients. Healing of the lesions was total at the end of the eight weeks of clinical observation in each patient.

The general health of the patients was very good without any complaints such as fever, asthma or anorexia. Thirty-one patients out of the 37 gained weight from 200 to 3800 grams during the treatment period. We saw no digestive, neurological, allergic, cardiovascular, or any other complications.

This work was performed in the medical facilities of the University of Bucharest.

The above has been offered for illustrative purposes only and is not intended to limit the scope of the invention of this application, which is as defined in the claims below.

That which is claimed is:

1. The method of treating a patient with acne by administering to said patient both orally and topically an effective amount of pharmaceutical compositions which comprise 0.5 to 40 weight per cent of an extract of propolis in a pharmaceutical dispersant, which comprises a neutral-buffered, plant extract-based emollient comprising an extract of verbascum and optionally an extract selected from the group consisting of Gratiola officinalis, millefoli, black honey comb, and combinations thereof.

2. The method of claim 1 in which an extract of verbascum is present in a concentration of 1 to 50 weight percent.

3. The method of claim 2 in which an extract of gratiola officinalis is present in a concentration of 1 to 50 weight percent.

4. The method of claim 2 in which an extract of millefoli is present in a concentration of 10 to 30 weight percent.

5. The method of claim 4 in which said pharmaceutical composition contains from 0.4 to 50 weight percent of propylene glycol as the dispersant.

6. The method of treating a patient with acne by administering enterally to the patient an effective amount of a first pharmaceutical composition which comprises 0.5 to 40 weight percent of an extract of propolis in a pharmaceutical carrier for enteral administration, which first composition further comprises from 5 to 50 weight percent of an extract of verbascum, 10 to 50 weight percent of an extract of gratiola officinalis, and 15 to 30 weight percent of a black honeycomb extract; while at the same time applying to skin portions of the patient exhibiting acne an effective amount of a second pharmaceutical composition which comprises 0.5 to 40 weight percent of an extract of propolis in a topical pharmaceutical carrier, which further comprises from 1 to 50 weight percent of an extract of verbascum; from 1 to 50 weight percent of an extract of gratiola officinalis; and from 10 to 30 weight percent of millefoli.

7. The method of claim 6 in which said second pharmaceutical composition is in the form of a lotion and comprises from 10 to 20 weight percent of a propolis extract, from 15 to 20 weight percent of an extract of verbascum; from 15 to 20 weight percent of an extract of gratiola officinalis; and from 15 to 20 weight percent of an extract of millefoli.

8. A pharmaceutical composition for oral administration which comprises 10 to 30 weight percent of an extract of propolis in propylene glycol, which composition also comprises an extract of verbascum in a concentration of 10 to 50 weight percent; from 10 to 50 weight percent of an extract of Gratiola officinalis; and from 15 to 30 weight percent of a black honeycomb extract.

9. A pharmaceutical composition for topical administration which comprises from 0.5 to 40 weight percent of an extract of propolis in propylene glycol, which composition also comprises 5 to 30 weight percent of an extract of verbascum; 10 to 30 weight percent of an extract of Gratiola officinalis; and 10 to 30 weight percent of an extract of millefoli.

* * * * *